US00PP12960P2

(12) United States Plant Patent
Drewlow

(10) Patent No.: US PP12,960 P2
(45) Date of Patent: Sep. 17, 2002

(54) NEW GUINEA IMPATIENS PLANT NAMED 'OVATION ORCHID STAR'

(75) Inventor: Lyndon W. Drewlow, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/550,520

(22) Filed: Apr. 17, 2000

(51) Int. Cl.[7] ..... A01H 5/00

(52) U.S. Cl. ..... Plt./318

(58) Field of Search ..... Plt./318

*Primary Examiner*—Bruce R. Campell
*Assistant Examiner*—Anne Marie Grünberg
(74) *Attorney, Agent, or Firm*—Webb Ziesenheim Logsdon Orkin & Hanson, P.C.

(57) ABSTRACT

A distinct cultivar of Impatiens plant named Ovation Orchid Star, characterized by its deep purple-violet bicolored flowers, large flower diameter, dark green leaves with red-purple casting, continuous, and long-lasting flowering, self-branching and vigorous habit.

1 Drawing Sheet

The present invention relates to a new and distinctive cultivar of Impatiens plant, botanically known as *Impatiens Hawkeri,* commercially known as New Guinea Impatiens, and known by the cultivar name 'Ovation Orchid Star'. Ovation Orchid Star was developed in a controlled breeding program by crossing Mikkelsen Seedling No. 94-604-1 (seed parent) with Mikkelsen Seedling No. 95-377-1 (pollen parent). The seed parent and the pollen parent are each a proprietary breeding line which have not been sold or made publicly available in this country.

Asexual reproduction carried out by the inventor in Lompoc, Calif. by terminal or stem cuttings has shown that the unique features of this new Impatiens are stabilized and are reproduced true to type in successive propagations.

The following combination of characteristics distinguishes the new Impatiens from both its parent varieties and other cultivated Impatiens of this type known and used in the floriculture industry:

1. Ovation Orchid Star has bicolored flowers with a deep Purple-Violet Group 80A while Guadeloupe (U.S. Plant Pat. No. 10,001) and Harmony Purple-Eyed (unpatented) both have Purple-Violet Group 82C colored flowers with Ovation Orchid Star having the most distinct bicolor area in the petals of Red-Purple Group 74C.

2. Ovation Orchid Star has a mounded growth habit whereas, Guadeloupe and Harmony Purple-Eyed are more upright.

3. Ovation Orchid Star is taller than Guadeloupe and similar in height to Harmony Purple-Eyed.

4. Ovation Orchid Star has dark green leaves with a heavy red-purple cast, while Guadeloupe and Harmony Purple-Eyed have dark green leaves with no red-purple cast.

5. The leaves of Ovation Orchid Star have a Greyed-Purple Group 187A underside color while Guadeloupe and Harmony Purple-Eyed have a red-purple cast underside leaf color.

6. Ovation Orchid Star has shorter leaves (8 to 9 cm) than Guadeloupe (9 to 10 cm) and has wider leaves (3.5 to 4.0 cm) than Harmony Purple-Eyed (2.5 to 3.0 cm).

7. Ovation Orchid Star has more anthocyanin in the stem than Guadeloupe and Harmony Purple-Eyed.

The accompanying colored photograph illustrates the overall appearance of this cultivar taken as a face view of the plant and showing the colors as true as it is reasonably possible to obtain in a colored reproduction of this type.

The following is a detailed description of my new cultivar, based on plants produced in greenhouses in Lompoc, Calif. during the Fall–Winter season of the year. Plants were grown in 15 cm pots and measurements were taken 20 weeks after rooted cuttings were planted. Height measurements were taken from the soil line of the container. The plants were grown at 16° C. night temperatures, under 3000 to 4000 foot candles of light and 200 ppm nitrogen, 75 ppm potassium, and 200 ppm phosphorous with nutritional trace elements added. Habit of growth, foliage coloration, leaf variegation, size of leaves and flower size will be greatly influenced by nutritional and environmental conditions.

Color references are made to The Royal Horticultural Society Colour Chart except where general terms of ordinary dictionay significance are used.

Parentage: A controlled cross between female parent Mikkelsen Seedling, 94-604-1 and male parent Mikkelsen Seedling No. 95-377-1.

Propagation:

(*A*) *Type cutting.*—Stem tip cuttings 15 mm long will develop to 4 to 5 cm long in 18 to 21 days.

(*B*) *Time to root.*—8–10 days at 23° C. summer; 10–12 days at 20° C. winter.

(*C*) *Rooting habit.*—Heavy, fibrous.

Plant description:

(*A*) *Form and habit of growth.*—Mounded, self-branching; intermediate in height; flowers open over the top of leaf canopy; continuous flowering; vigorous growing flowering herb. Average plant height is 18 to 22 cm, and average width is 45 to 50 cm. Internode length is 5 to 6 cm, but is highly variable, with a color of Yellow-Green Group 146B with a Greyed-Purple Group 184A cast.

(*B*) *Foliage description.*—Dark green with red-purple cast; red-purple midrib and no leaf variegation. The young midrib underside is Greyed-Purple Group 185A, and the mature midrib underside is Greyed-Purple Group 185B, mature leaf color is Yellow-Green Group 147A, with a Greyed-Purple Group 187A cast. Stem color is Yellow-Green Group 146B, with a Greyed-Purple Group 184A cast. (1) Size: 8 to 9 cm long and 3.5 to 4 cm wide on average mature leaf. (2) Shape: Lanceolate with acuminate apex and acute base. (3) Texture: Both upper and lower surfaces are glabrous. (4) Margin: Entire, with fine ciliate. (5) Color: Young foliage, top side is Yellow-Green Group 147A with a Greyed-Purple Group 187A cast, underside is Greyed-Purple Group 187A. Mature foliage, top side is Yellow-Green Group 147A with a Greyed-Purple Group 187A cast, underside is Greyed-Purple Group 187A. (6) Venation: Pinnate. Young and mature venation underside is Greyed-Purple Group 185A.

(*C*) *Branching.*—Lateral branching at base: 5 or more. Lateral branch length is 12 to 15 cm, but is highly variable.

Flowering description:

(*A*) *Flowering habits.*—Flowers continuously from leaf whorl in a progressively orderly manner with one flower per leaf axil. When the last flower in a whorl opens, the first flower in the leaf whorl above starts to open. It takes 5 to 7 days for a mature bud to fully open and the flower may last two weeks or longer depending on the environment. The time to first flower is 50 to 55 days from rooted cutting. The flowers are self-cleaning.

(*B*) *Natural flowering season.*—Indeterminate and continuous; quantity of flowering increases with increasing levels of light.

(*C*) *Flower bud.*—Ellipsoidial; flowers perfect; spur is Yellow-Green Group 147D, with a Greyed-Purple Group 185D cast, near major sepal with Yellow-Green Group 146B tip and is 5.5 cm long on average on mature bud, with the throat behind the ovary and originating from the major sepal. The pedicel is Yellow-Green Group 146B, the throat is Red Group 47A, and the bud is Purple-Violet Group 80A, just before opening.

(*D*) *Flowers borne.*—On individual yellow-green pedicels 3.5 cm long from a whorl of usually five leaves. Flowering progressively around the whorls as buds and leaves develop. Leaf axils have one flower each.

(*E*) *Quantity of flowers.*—Numerous because of self-branching nature of plant and the long-lasting flower characteristic.

(*F*) *Diameter of flower.*—6.5 to 7 cm. Flower depth: 5 mm.

(*G*) *Petals.*—(1) Shape: Heart; standard petal is largest. (2) Color: Top side in winter when opening is Purple-Violet Group 80A with Red-Purple Group 74D in center, especially on standard petal; fading to Purple-Violet Group 80B with Red-Purple Group 74A at center; underside is Red-Purple Group 74C with Red Group 47A in the center and in center of standard petal. (3) Number of petals: Five. (4) Size of petals: Standard: 4.0 cm wide and 3.0 cm long, equal lobes with moderate cut. Wings: 3.0 cm wide and 3.0 cm long, unequal lobes with shallow cut. Keel: 3.5 cm wide and 3.0 cm long, unequal lobes with moderate cut.

(*H*) *Reproductive organs.*—(1) Stamens: Five in number. (a) Anther: Hooded shape, color is Yellow-White Group 158B, with a Red-Purple Group 63A cast. (b) Pollen color: Yellow-White Group 158C. (2) Pistils: (a) Stigma: Five, segmented column, Greyed-Purple Group 185B. (b) Style color: Red-purple. (c) Ovaries: Five in number, size is 5 mm when immature, color is Yellow-Green Group 146A, with a Greyed-Purple Group 185C cast.

(*I*) *Fertility.*—The plants are fertile, but not normally set seed under greenhouse conditions, unless in a controlled breeding program.

Disease resistance: No significant disease or insect problems seen to date.

OTHER IMPORTANT CHARACTERISTICS

1. Self-branching, early flowering nature allows cultivar to be grown in 10 cm pots but is also vigorous enough to be grown in 15 to 25 cm containers as well.

2. Minimal fading of older flowers and large overlapping petals result in a round flower that produces an attractive floral display.

3. Has shown the ability to tolerate both high temperatures and full sun and continue to bloom as demonstrated in Connellsville, Pa. summer trials and to bloom as well with cool night temperatures (5 to 10° C.) as demonstrated in outdoor trials in Lompoc, Calif., thus, extending the growing season.

I claim:

1. A new and distinct variety of Impatiens plant named Ovation Orchid Star, as illustrated and described.

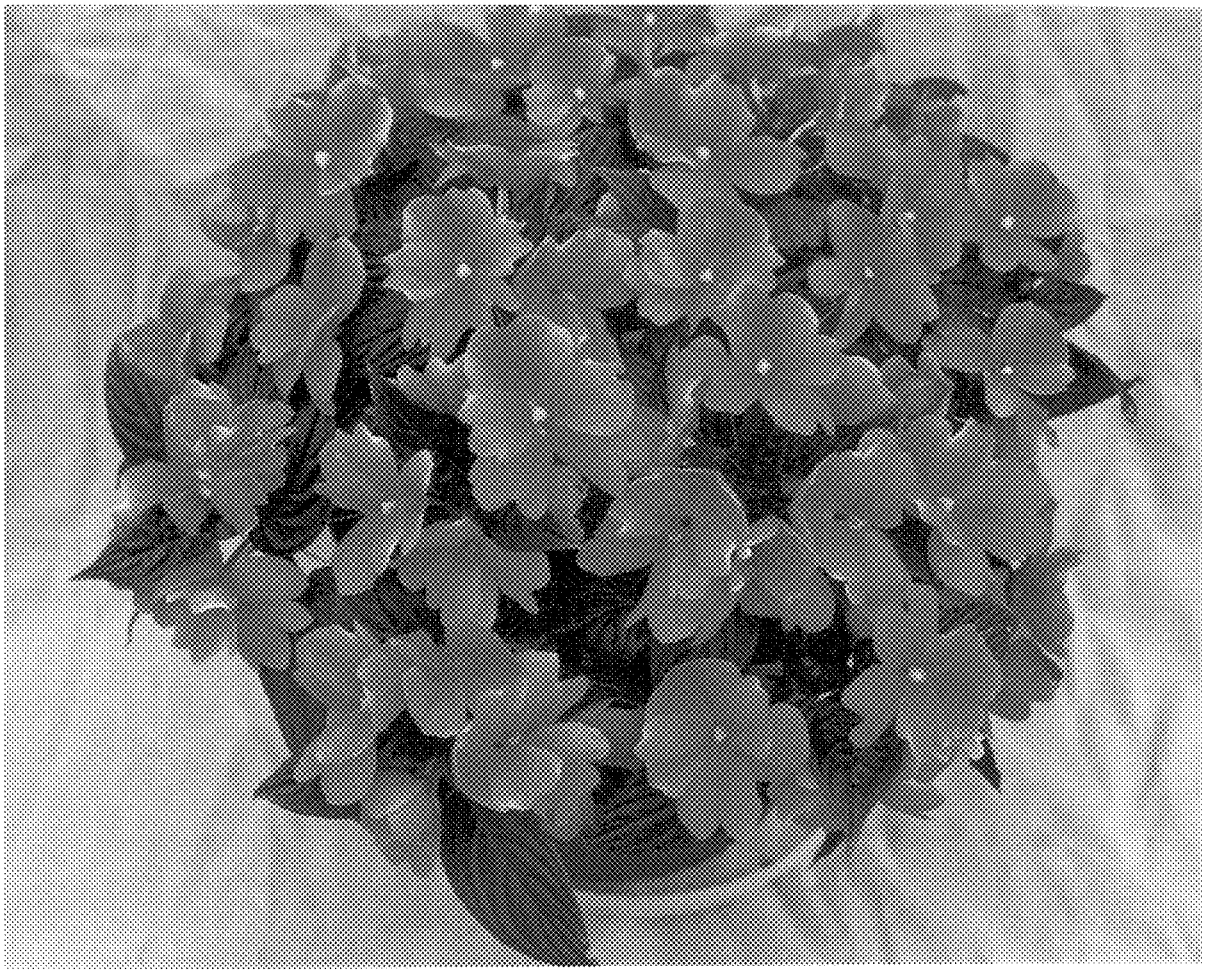

* * * * *